United States Patent
Wilhelm et al.

(10) Patent No.: US 11,738,032 B2
(45) Date of Patent: *Aug. 29, 2023

(54) PHARMACEUTICAL FORMULATION FOR THE TREATMENT OF INFLAMMATORY CHANGES TO THE RECTUM

(71) Applicant: Dr. Falk Pharma GmbH, Freiburg (DE)

(72) Inventors: Rudolph Wilhelm, Bischweier (DE); Markus Pröls, Freiburg/Breisgau (DE); Roland Greinwald, Kenzingen (DE); Ralf Mohrbacher, Freiburg (DE)

(73) Assignee: Dr. Falk Pharma GmbH, Freiburg (DE)

( * ) Notice: Subject to any disclaimer, the term of this patent is extended or adjusted under 35 U.S.C. 154(b) by 304 days.

This patent is subject to a terminal disclaimer.

(21) Appl. No.: 17/094,233

(22) Filed: Nov. 10, 2020

(65) Prior Publication Data

US 2021/0100819 A1    Apr. 8, 2021

Related U.S. Application Data

(63) Continuation of application No. 15/742,710, filed as application No. PCT/EP2016/064907 on Jun. 28, 2016, now Pat. No. 10,905,699.

(30) Foreign Application Priority Data

Jul. 8, 2015 (EP) .................... 15175806

(51) Int. Cl.
| | |
|---|---|
| *A01N 37/00* | (2006.01) |
| *A61K 31/215* | (2006.01) |
| *A01N 37/12* | (2006.01) |
| *A01N 37/44* | (2006.01) |
| *A61K 31/24* | (2006.01) |
| *A01N 25/00* | (2006.01) |
| *A61K 31/58* | (2006.01) |
| *A61K 9/02* | (2006.01) |
| *A61K 31/606* | (2006.01) |
| *A61P 29/00* | (2006.01) |

(52) U.S. Cl.
CPC ............ *A61K 31/58* (2013.01); *A61K 9/02* (2013.01); *A61K 31/606* (2013.01); *A61P 29/00* (2018.01)

(58) Field of Classification Search
None
See application file for complete search history.

(56) References Cited

U.S. PATENT DOCUMENTS

| | | | | |
|---|---|---|---|---|
| 3,208,907 A | * | 9/1965 | Delarue | .............. A61K 47/22 514/161 |
| 4,871,777 A | * | 10/1989 | Breitzke | .............. A61K 9/02 424/502 |
| 5,858,998 A | | 1/1999 | Leuschner | |

FOREIGN PATENT DOCUMENTS

| | | |
|---|---|---|
| DE | 297 17 252 U1 | 2/1998 |
| DE | 198 49 737 A1 | 5/2000 |
| GB | 701831 A | 1/1954 |
| WO | WO 00/24388 A2 | 5/2000 |
| WO | WO 2008/156671 A2 | 12/2008 |
| WO | WO-2012022796 A2 * | 2/2012 ........... A61K 31/495 |

OTHER PUBLICATIONS

International Search Report in PCT/EP2016/064907, dated Aug. 25, 2016.
International Written Opinion in PCT/EP2016/064907, dated Aug. 25, 2016.
International Preliminary Report on Patentability in PCT/EP2016/064907, dated May 29, 2017.

* cited by examiner

*Primary Examiner* — Layla Soroush
(74) *Attorney, Agent, or Firm* — Curatolo Sidoti & Trillis Co., LPA; Salvatore A. Sidoti; Floyd Trillis, III

(57) ABSTRACT

Disclosed is a storage-stable pharmaceutical formulation for rectal administration, containing budesonide or a pharmaceutically compatible salt or derivative thereof, and at least 80 wt % of a solid fat or a mixture of different solid fats, based on the total weight of the formulation, as well as at least one anti-oxidation agent that is compatible therewith.

18 Claims, 1 Drawing Sheet

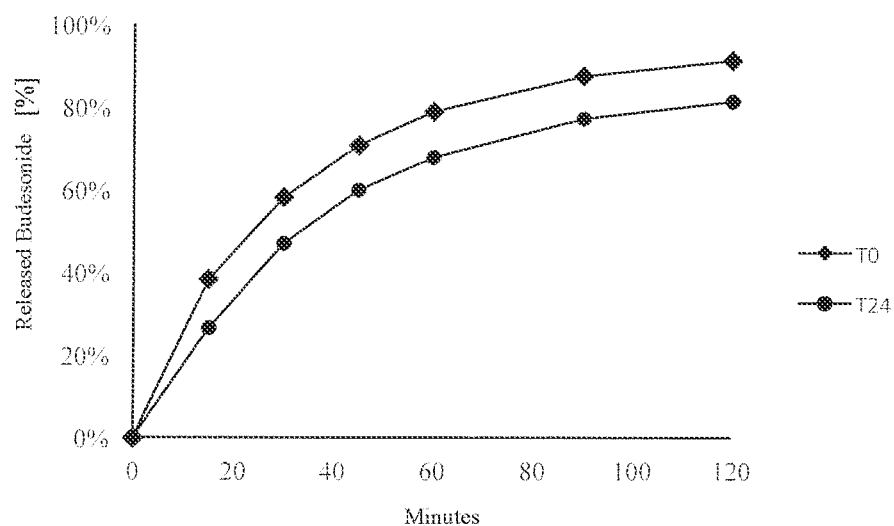

PHARMACEUTICAL FORMULATION FOR THE TREATMENT OF INFLAMMATORY CHANGES TO THE RECTUM

The present application is a continuation of co-pending U.S. Ser. No. 15/742,710, filed Jan. 8, 2018, which is a U.S. National Stage application under 35 U.S.C. § 371 of International Application No. PCT/EP2016/064907, filed Jun. 28, 2016, which claims priority from European Patent Application No. 15175806.7, filed Jul. 8, 2015, which applications are hereby incorporated herein by reference.

Chronic inflammatory diseases of the gastro-intestinal tract are referred to as the Crohn's disease as well as ulcerative colitis. The etiology of said diseases is unknown, although an autoimmune aspect of said diseases is often assumed. The disease "Crohn's disease" may contain a variety of clinical manifestations and said disease can be located in different parts of the small intestine as well as of the large intestine. Ulcerative colitis is an inflammatory intestinal disease that is substantially confined to the large intestine. The disease is characterized by recurrent inflammatory conditions that primarily affect the mucosa layer and occasionally also the submucosa layer of the colon. Acute inflammatory conditions are characterized by chronic diarrhea or constipation, bleeding in the intestinal tract, cramps and stomachache.

Occasionally, a distinction is made regarding ulcerative proctitis, which is regarded as a milder form of ulcerative colitis. For the therapy of said diseases specifically formulated formulations for oral administration can be used. However, oral administration may be disadvantageous due to the diarrhea often associated with the disease.

In the prior art there are also known rectally administrable formulations. Gross et al., Aliment. Pharmacol. Ther. 2006, 23, 303-312 in the treatment of active ulcerative proctitis or proctosigmoiditis have compared budesonide foams with budesonide enemas.

Belluzzi et al. (Gastroenterology, Vol. 104 (4, Suppl.) 1993) have suggested suppositories with 5-aminosalicylic acid or budesonide. The budesonide suppositories used there contained 0.5 mg budesonide and were given three times a day. Alternatively, suppositories with 500 mg 5-aminosalicylic acid were given three times a day.

U.S. Pat. No. 5,449,520 discloses pharmaceutical compositions for the rectal administration, which contain a medicament topically active on the colon. The rectal foams disclosed there contain as a pharmaceutical active ingredient mesalazine or budesonide. WO 2015/073846 describes a method for the treatment of ulcerative colitis in which a rectal foam is employed. The foam is an emulsion containing budesonide, propylene glycol, cetyl alcohol, water, and suitable additives.

In the German utility model DE 297 17 252 there is disclosed a medical drug kit of a budesonide-containing and an ursodeoxycholic acid-containing medical drug for the treatment of cholestatic hepatic diseases. One formulation example relates to budesonide-containing suppositories, wherein budesonide is suspended in solid fat.

DE-OS 198 49 737 discloses suppositories containing an active ingredient combination consisting of 5-ASA and budesonide suspended in solid fat. Due to the high proportion of 5-ASA these suppositories have a relatively high weight and thus, also a corresponding size.

A disadvantage of the known pharmaceutical formulations on the one hand is that some patients dislike to use enemas or also rectal foams. Another requirement is that a pharmaceutical formulation is desired that provides the active ingredient budesonide in a storage-stable form.

It is a task of the present invention to provide a pharmaceutical formulation of budesonide for the rectal application that is storage-stable and that allows painless insertion by an optimum form, consistency and suitable size as well as a specific, local and rectum-confined application of the active ingredient.

According to the invention, these criteria are fulfilled by the administration in the form of turundula also referred to as suppository. Suppositories contain a single dose of the medicinally effective component budesonide that can be dissolved (solution preparation), emulsified (emulsion preparation) and suspended (suspension preparation) in a lipid-containing or water-soluble preparation.

The pharmaceutical formulations according to the invention are highly storage-stable. A problem with the provision of suppositories (turundulas) is that when such preparations are stored at room temperature or a slightly increased temperature (20-30° C.), which often occurs during the summer months or in warmer areas, the pharmacologically active ingredient budesonide is decomposed to biologically inactive or less active decomposition products. The formulations according to the invention are storage-stable over a longer period of time (12-24 months) also at an increased temperature (20-30° C.). This means, that after storage over 24 months at 25° C. still at least 90%, preferably at least 95% and preferably at least 97% of the originally employed active ingredient (budesonide) are present in a pharmacologically active form.

The present invention relates to a preparation for the rectal use, particularly a suppository, that includes as the therapeutically effective component budesonide or a pharmaceutically compatible salt or derivative thereof and after insertion is used for the treatment of inflammatory diseases of the rectum (proctitis). In doing so, high demands must be made on the selection of a suitable basis. This basis has to be chemically stable and inert and therefore highly compatible with the medicinally effective component, as well as compatible with mucous membranes and therefore free of mucosal irritation during application. Further, it has to reliably release the intermingled medicinally effective component at the place of use after application by melting or dissolving.

Thus, the object of the present invention is a storage-stable pharmaceutical formulation for rectal administration, containing budesonide or a pharmaceutically compatible salt or derivative thereof, and at least 80 wt % of a solid fat or a mixture of different solid fats, based on the total weight of the formulation, as well as at least one anti-oxidation agent that is compatible therewith.

In a preferred embodiment of the present invention there is chosen a solid fat composition having a small distance between the melting and freezing point. The melting point is the temperature at which the suppository melts. Said melting point is preferably between about 33.5° C. and about 35.5° C., preferably between 34.0° C. and 35.0° C. The freezing point is the temperature at which the suppository freezes after manufacture, i.e. the point at which the suppository solidifies after manufacture. According to the invention, said freezing point is preferably between about 32.5° C. and 34.5° C., particularly preferred 33.0° C. to 34.0° C.

In a preferred embodiment, the solid fat employed according to the invention has a high proportion of triglycerides that is preferably above 80 wt %, particularly preferred above 90 wt %, and especially preferred above 95 wt. %.

As a parameter of said solid fats there is known the so-called hydroxyl value. According to invention the solid fats employed have a low hydroxyl value that is in the range of from 1 to 15, preferably 5 to 15, and particularly preferred 5 to 10.

A further property of the preferred solid fats is that the proportion of the unsaturated fatty acids is less than 1 wt %, particularly preferred less than 0.5 wt %.

The suppositories according to the invention are designed for anal administration. Thus, the form is chosen such that they can be conveniently applied and are considered well acceptable by the majority of patients because they neither cause pain nor an unpleasant feeling when administered. In a preferred embodiment the suppositories have a so-called "torpedo shape". Also important is the size of the suppositories that is determined by the total weight of the suppositories. Preferably, the weight is between 0.8 g and 1.2 g, particularly preferred between 0.95 g and 1.05 g.

In a preferred embodiment the suppository according to the invention as the active ingredient contains budesonide in an amount between 1.8 mg and 2.2 mg per suppository, preferably between 1.9 mg and 2.1 mg budesonide per suppository and especially preferred between 1.95 mg and 2.05 mg budesonide per suppository.

In another preferred embodiment the suppository according to the invention as the active ingredient contains budesonide in an amount between 3.8 mg and 4.2 mg per suppository, preferably between 3.9 mg and 4.1 mg budesonide per suppository and especially preferred between 3.95 mg and 4.05 mg budesonide pro suppository.

According to the invention, it is preferred that the suppository as the pharmacologically active ingredient only contains budesonide and no other pharmacologically active component. In particular, the suppositories according to the invention especially preferred contain no 5-ASA (5-aminosalicylic acid). Since 5-ASA itself is oxidation-sensitive the addition of 5-ASA could result in an undesired brown coloration of the suppository.

In a preferred embodiment, the suppositories according to the invention as the anti-oxidation agent contain ascorbyl palmitate. The concentration of the ascorbyl palmitate is preferably 50 ppm to 200 ppm, particularly preferred 125 to 175 ppm, and especially preferred 150 ppm.

A further preferred aspect of the present invention is that the budesonide is present in a micronized form. Micronized form means that the particle size of the active ingredient is very small, wherein 100% of the particles are smaller than 10 µm per particle.

An essential aspect of the present invention is the storage stability of the suppositories according to the invention. The storage stability can be further enhanced by various process steps during manufacture. On the one hand, the manufacture of the suppositories can be carried out under exclusion of oxygen. This can be achieved by nitrogen purge during manufacture or working under inert-gas atmosphere.

On the other hand, the melted mass is preferably poured into a blister foil during the production of the suppositories, where the hardening takes place. In a preferred embodiment the suppositories according to the invention are packed in a gas-tight film.

It is generally known to use lipid-containing or water-soluble preparations as the basis for suppositories. Preferably, triglycerides are used as the lipids. Solid fat is a semi-synthetic mixture of mono-, di-, and triglycerides of saturated fatty acids. Starting from palm kernel oil and coconut butter defined solid fats having certain melting properties and certain hydroxyl values can be obtained after saponification and re-esterification of glycerin with suitable saturated fatty acids via the ratio of mono-, di-, and triglycerides. Thus, by the choice of fatty acids and the degree of esterification the properties of solid fat can be modified and properties such as melting range, water-absorbing capacity, and brittleness can be influenced. By the lack of unsaturated fatty acids solid fats have better stability properties than cocoa butter, which therefore only plays a minor role as a suppository basis.

The choice of the suitable solid fats plays an important role for achieving the required storage stability. Thus, preferably the solid fats described here are employed, wherein a crucial aspect is to achieve the desired storage stability. To achieve the storage stability particularly also the ratio of budesonide (active ingredient) to solid fat is essential.

The solid fats preferably used according to the invention are based on glycerides of saturated $C_{12}$-$C_{18}$ fatty acids. They largely consist of triglycerides containing not more than 15% of diglycerides and not more than 1% of monoglycerides. In the manufacture of the solid fats according to the invention at first vegetable fats are decomposed into fatty acids and glycerin after purification by means of water at high temperature. The fatty acid blend is hydrogenated, fractionated, and vacuum-distilled, above all to remove short-chain fatty acids. The $C_{12}$-$C_{18}$ fatty acids preferably used are adjusted to a suitable blend and esterified with purified glycerin. Said reaction blend is subsequently further purified, in particular by washing, vacuum drying, treating to remove dyes, and steam distillation. The preferably used hard waxes contain at least 85%, preferably at least 90%, of $C_{12}$-$C_{18}$ fatty acid chains. It is also important that the hydroxyl value of the solid fats is preferably less than about 10. The hydroxyl value is mainly due to the monoglycerides, since these provide two hydroxyl groups from the glycerol residue, and diglycerides, which have a free hydroxyl group. The hydroxyl value can be measured by determining the amount of KOH that is required to neutralize the amount of acetic acid that is consumed by the acetylation of the solid fat. That is, the hydroxyl value denotes the amount of the free hydroxyl groups in the solid fat basis. Since the solid fats employed according to the invention are usually released during the purification of glycerin the hydroxyl value is an indicator for the presence of mono- and/or diglycerides that are present in the solid fat blend. Provided that further additives are present in the solid fat blend that contribute to the free hydroxyl groups they also influence the hydroxyl value.

A further important characteristic of the solid fats according to the invention is the iodine value. The iodine value represents the amount of grams of halogen (iodine) that is consumed by 100 g of the solid fat blend. For the consumption of halogen unsaturated compounds, i.e. unsaturated fatty acids, are responsible. Since, according to the invention, this proportion is very low, the iodine number for the qualities to be used is less than 3, preferably less than 2.

An essential parameter of the suppository basis is also the peroxide value. This value reflects the amount of peroxide in milliequivalents of active oxygen that are present in 1000 g of the suppository basis. In the suppository basis used according to the invention the peroxide value, given in meq O/kg, is at most 5, preferably at most 3, and particularly preferred at most 1.

In addition to the lipid-containing suppository bases also water-soluble macrogol-based masses are used that dissolve in the rectally present liquids. Preferably, macrogol 6000 or blends of high and low molecular masses are employed. The proportions of macrogol-based additives are between 0 and 20, preferably between 0 and 5, and particularly preferred at 0.1 to 3 wt %, based on the finished formulation. If such components are used, care must be taken to ensure a low peroxide value of at most 5 meq O/kg.

Budesonide is a glucocorticoid having a high local anti-inflammatory efficacy. The substance is virtually insoluble in water (0.014 mg/ml, Merck Index), however, due to its lipophilic properties appreciable amounts dissolve in organic solvents such as ethanol, methanol, and chloroform. Depending on the medium used the dissolved substance is more or less instable. Said instability is also a consequence of an oxidative degradation of budesonide. Thus, without any further measure the generally known application of lipid-containing or water-soluble bases is not an option for the manufacture of stable and compatible budesonide suppositories, since the medicinally effective component dissolved in those vehicles is rapidly degraded.

As described in example 1, simple budesonide suppositories of solid fat of different quality (Witepsol® H15, Witepsol® W45) already after a 3 months storage at 25° C./60% relative humidity show a ca. 10% reduction in content. Blends of budesonide with macrogols are per se incompatible due to the peroxides inherently present in traces or formed in this matrix, respectively, and do not represent an alternative for the treatment of inflammatory diseases of the rectum because of the local irritation of the mucosa said suppositories cause after application.

In comparison, the budesonide suppositories according to the invention do not show the drawbacks underlying the prior art. The present invention is only made possible by a combination of measures, i.e. at least two, preferably at least three of the measures listed below, each of which is not sufficient to achieve the specified aim.

Thus, the object of the present invention are stable and compatible budesonide suppositories that can be obtained by the following measures:
(a) the use of budesonide as a medicinally effective component in a suitable particle size distribution,
(b) the choice of a suitable solid fat quality,
(c) the addition of ascorbyl palmitate as an antioxidant to the solid fat basis in an optimized concentration,
(d) the adjustment of an optimum ratio of budesonide dissolved as well as suspended in the solid fat basis,
(e) the use of a suppository form and size, respectively, suitable for the described application; and
(f) the use of a cast film of low oxygen permeability as a package.

Preferably, two or more of said measures (i.e. 3, 4, 5, or 6) are combined.

The budesonide suppositories composited and prepared in accordance with the application according to the invention have sufficient stability allowing the storage and application of the suppositories at environmental conditions of 25° C./60% relative humidity for at least 24 months. At the same time, it is ensured by the invention that the application of the suppositories for the treatment of the indication according to the invention due to their size and form can be without pain and that, after the insertion of the suppositories, the proportion of suspended medicinally effective component rapidly sediments from the molten basis to the affected mucous membrane sites, while the dissolved proportion is distributed from the basis. This ensures that both patient's compliance and efficacy of budesonide is made possible over a sufficiently long period of time.

For the preparation of stable budesonide suppositories particularly suitable are lipophilic bases of the solid fat type. Solid fat types with a high proportion of triglycerides (at least ca. 85%) and thus, low hydroxyl value (5-15) have proved to be especially preferred. Solid fats basically consist of a mixture of different mono-, di-, and triglycerides. Depending on the composition of the solid fat this results in a different number of free OH groups, which in turn results in different properties. Thus, one characteristic for solid fats is the hydroxyl value. Most important are solid fat types with hydroxyl values<15. Because of the small number of free OH groups there hardly occur incompatibilities with hydrolysis-sensitive substances or substances with free acid groups in those suppository bases. In comparison, generally solid fats with a high hydroxyl value have a good emulsifiability and hardly any cracking during freezing. However, a tendency to post-hardening can be observed and incompatibilities with the active ingredient are possible. However, solid fats with a low hydroxyl value of <15 have a low emulsifiability, more often tend to cracking during freezing and show low tendency to post-hardening.

According to the invention, preferably solid fat types are employed which contain as little or no unsaturated fatty acids as possible, because unsaturated compounds often are subject to oxidation reactions and can rancidify. The number of unsaturated bonds in a lipid can be established by the iodine value (Ph. Eur. 2.5.4).

Solid fat consists of a blend of mono-, di-, and triglycerides. By variations in the composition and the esterified fatty acids the melting point of the solid fat can be changed.

A preferably employed conventional type is Witepsol® H 15. Said particularly preferred quality mainly contains saturated fatty acids (iodine value 3), is characterized by a small distance between melting (33.5-35.5° C.) and freezing point (32.5-34.5° C.), and has only a low tendency to post-hardening after pouring out. Using this basis ensures that the budesonide suppositories melt at body temperature and release the active ingredient.

It has surprisingly been shown that only a combination of active ingredient molecularly disperse dissolved as well as suspended in the particularly preferred solid fat quality allows the manufacture of storage-stable budesonide suppositories. This optimized combination of solution and suspension preparation in a suppository permits that further measures for stabilization only have to be limited to the solved proportion of the active ingredient. As described in example 2, the solubility of budesonide in the particularly preferred solid fat quality Witepsol® H 15 is 1.5 mg/g. With this saturation concentration it is possible to calculate the dose solubility of the active ingredient in the basis and thus, to selectively choose the amount of antioxidant required for stabilization.

At a budesonide dose of 2 mg or 4 mg, respectively, and a suppository mass of 1.8 g for the 2 mg form 100% of the dose are present molecularly disperse dissolved (pure solution suppository), whereas for the 4 mg form the dissolved proportion is 67.5% (combined variant of solution and suspension suppository).

Thus, preferably the weight ratio of budesonide to suppository mass (in total) is between 1-10 to 1000 and particularly preferred between 1-5 to 1000.

Only the reduction of the suppository mass from 1.8 g to 1 g that is preferred according to the invention makes it possible to realize the combined suppository variant for the desired dose range of 2 mg to 4 mg. In the case of the budesonide 2 mg suppositories then 75% of the dose are present in a dissolved form and 25% in a suspended form. For the budesonide 4 mg suppositories the ratio is 37.5% (dissolved proportion) and 62.5% (suspended proportion). This ensures that an optimum concentration of antioxidant can be added, which exerts the stabilizing effect exclusively on the dissolved active ingredient proportion of 37.5% to 75.0%. Only this surprisingly found complex interaction of physical and chemical stabilization of the preparation permits the long-term stability of budesonide suppositories at environmental conditions and thus, the renouncement of a storage in a refrigerator.

With the reduction of the mass from 1.8 g to about 1 g the budesonide suppository at the same gets a size and shape that are particularly preferred for the application so that insertion without any pain can be ensured.

The suppositories according to the invention have a weight of about 0.8 to 1.2 g, preferably 0.9 to 1.1 g, and particularly preferred 0.95 to 1.05 g.

As described in example 1, the active ingredient proportion that is molecularly disperse dissolved in the solid fat basis has to be stabilized by the addition of an anti-oxidatively acting excipient. Antioxidants are a group of excipients acting as free-radical scavengers or as substances that are easily oxidizable and thus, can protect the active ingredient from oxidation.

Now it has been surprisingly found that only ascorbyl palmitate proves to be suitable for the stabilization among the antioxidants such as ascorbyl palmitate, DL-α-tocopherol, and butylated hydroxyanisole that are usually employed in non-aqueous, lipophilic systems. Example 3 shows the results of the selection attempts. What is striking is that the excipients DL-α-tocopherol, and butylated hydroxyanisole in contrast to the actually desired antioxidative effect even enhance the degradation of budesonide in the solid fat basis.

The use of ascorbyl palmitate in a concentration range of 50 ppm to 250 ppm has been shown to be particularly suitable. Example 4 shows the concentration-related effect of ascorbyl palmitate on the contamination profile of budesonide 2 mg suppositories during a storage period of 24 months at 25° C./60% relative humidity. In comparison to the unstabilized budesonide suppositories of example 1 only this measure allows a long-term stabilization of the active ingredient proportion dissolved in the solid fat, wherein preferably a concentration range of 100 ppm to 200 ppm of ascorbyl palmitate is effective. With the described reduction of the suppository mass to 1 g as well as the optimized addition of ascorbyl palmitate of 100 ppm thus, budesonide suppositories can be prepared that are stable for at least 24 months at 25° C./60% relative humidity and do not need to be stored in a refrigerator.

In example 5 the composition of the preferred embodiments of budesonide 2 mg and 4 mg suppositories is described. Here, the molten suppository mass is poured into casting molds of plastic in which the mass subsequently rapidly solidifies. The dosage is volumetric for each individual suppository.

The laminated films used to receive the melt preferably consist of 100 μm thick polyvinylchloride films (LDPE/PVC/PVdC) coated with polyvinylidene chloride (40 g/m$^2$) and polyethylene of low density (40 μm). This casting mold is a package having an enhanced barrier function against oxygen and represents an additional protective mechanism for the formulation. The barrier protection can still be enhanced when casting molds of aluminum foil are selected for the budesonide suppositories.

In a preferred embodiment the suppositories according to the invention are completely prepared under nitrogen atmosphere. This means, that after having composited the individual components of the finished pharmaceutical formulation air is evacuated and subsequently, it is gassed with nitrogen or inert gas so that no oxidative reactions can take place. Then, the molten suppository mass with active ingredient is directly brought into the prepared gas-tight laminated films where they harden. Here, the laminated films are designed such that they prescribe the finished suppository shape and after being filled can be closed such that an oxygen contact with the suppository mass can largely be avoided.

By the measures according to the invention budesonide suppositories can be prepared that are storage-stable at room temperature. The results of the shelf life tests of example 6 prove impressively that the selected combination of stabilizing measures and protective mechanisms makes it possible to provide stable budesonide suppositories.

The particle size of the active ingredient budesonide should be as small as possible. For that, the budesonide is micronized in a suitable mill (e.g. jet mill). According to the invention, the micronization is carried out such that 100% of the particles are smaller than 10 μm. The micronized budesonide is intermingled into the molten solid fat via the powder feeding station of an inline homogenizer. Here, particle aggregates are milled and an even distribution of the undissolved proportion of the active ingredient in the basis is achieved. The reduction of the particle size is also a suitable means to prevent active ingredient sedimentation from the beginning. It is also important that the particles do not congregate. The risk of particle agglomeration is generally the larger the smaller the particles are, since with a decreasing particle size the surface area of the individual particles increases and thus, the surface energy increases. By adding a small amount of surfactants (typically less than 0.5 wt %, based on the micronized budesonide preparation) the risk of particle growth can be prevented. The addition of a surfactant can also result in an improved spreading and wetting of the active ingredient in the rectal fluid. However, it is important that a surfactant is chosen that does not cause any undesired side reaction in the administration of the suppositories.

For the therapeutic use the medicinally effective component budesonide is used in dosages of 2 mg to 4 mg. Here, the active ingredient is used in the micronized form, wherein 100% of the particles are smaller than 10 μm, at least 95% are smaller than 5 μm and at least 80% are smaller than 3 μm. The determination of the particle size distribution of budesonide takes place by laser diffraction analysis (laser diffractometry). Here, budesonide is wet-dispersed in an aqueous medium. After radiation of the particles with a monochromatic laser light the diffraction pattern is determined from which subsequently the particle size distribution can be calculated. The use of a micronized quality prevents the sedimentation of suspended budesonide in the molten suppository mass during the manufacture and thus, permits the even active ingredient distribution in the poured out and frozen molds. At the same time the micronization increases the dissolution rate of the budesonide, which has sedimented to the mucosa, in the rectal fluid after inserting and melting of the suppositories. Example 7 shows the results of in vitro releasing tests of budesonide 2 mg suppositories over a period of 2 hours. Within this period, both the suspended proportion of the active ingredient and that dissolved in the solid fat basis is released. Thus, with the formulation according to the invention it is ensured that the entire budesonide dose is released from the formulation and is available over a sufficiently long period of time on the rectal mucosa and thus, a therapeutic effect is achieved.

The suppositories according to the invention are preferably used for the treatment of inflammatory diseases of the rectum. These are preferably acute diseases for which a rapid relief of the symptoms is desirable.

The suppositories according to the invention are preferably used for the treatment of patients with active ulcerative proctitis. In a preferred embodiment a suppository with 2 mg budesonide or a suppository with 4 mg budesonide is administered once in the morning and once in the evening. Thus, the budesonide suppositories according to the invention are particularly suitable for the treatment of active ulcerative proctitis.

In a clinical study on patients with acute ulcerative proctitis in which embodiments of the present invention were studied alone or as combination therapy with conventional mesalazine suppositories in comparison to conventional mesalazine suppositories it could be demonstrated that the use of the budesonide suppositories according to the invention led to a significant reduction in the time until clinical symptoms disappeared. This end point was defined in the clinical study as the first day of three consecutive days with a point score of 0 for rectal bleeding and the frequency of defaecation.

The rate of patients that showed a clinical and endoscopic remission or an improvement in their symptoms was higher in those treated with budesonide suppositories. Clinical and endoscopic remission was achieved when the patients in the modified DAI-UC index (Disease Activity Index-Ulcerative Colitis) had a value of ≤1, wherein the result in the categories rectal bleeding and frequency of defaecation had to be 0 and at least 1 point of reduction in the sub-category "appearance of the mucosa" had to be achieved. An improvement of the symptoms required at least a reduction of the total score of ≥3 points.

Handling of the budesonide suppositories according to the invention with reduced suppository mass in patients also achieved a higher tolerance compared with mesalazine suppositories that were tested as comparative preparation.

In a special embodiment of the present invention the budesonide suppositories according to the invention are used during a combination therapy with mesalazine suppositories. Such a combination therapy preferably is that each in the morning there is administered a budesonide suppository and in the evening a mesalazine suppository or that in the morning a mesalazine suppository is administered and in the evening a budesonide suppository.

To evaluate the efficacy of the suppositories the modified UC-DAI evaluation standard as by Kamm et al. (2007, Gastroenterology, 132, p. 66-75) is used. It is explicitly referred to the table 1 disclosed there and the relating definitions of the parameters.

Preferred embodiments of the present invention are illustrated by the following examples.

EXAMPLE 1

Influence of the Solid Fat to the Degradation of Budesonide in Solid Fat of Different Qualities without Stabilization

TABLE 1

| Batch | Composition | | Initially | Content [%] 3 months 25° C./60% rel. humidity | 3 months 30° C./65% rel. humidity |
|---|---|---|---|---|---|
| V1860 | Budesonide | 2 mg | 96.2 | 86.6 | 75.3 |
|  | Witepsol ® H15 | 1798 mg | | | |
|  | Total: | 1800 mg | | | |
| V1866 | Budesonide | 2 mg | 94.4 | 77.5 | 70.2 |
|  | Witepsol ® W45 | 1798 mg | | | |
|  | Total: | 1800 mg | | | |

Without any further stabilizing measures budesonide 2 mg suppositories of the solid fat type are instable, wherein also the nature of the solid fat used has influence on the stability. Already after a storage period of 3 months a reduction in content of 10% and more is shown at 25° C./60% relative humidity. Here, the stability of budesonide with the solid fat type Witepsol® W45 is clearly less favorable than with the quality Witepsol® H15. Due to the small proportion of mono- and diglycerides Witepsol® H15 has a low hydroxyl value, while Witepsol® W45 has a higher proportion of mono- and diglycerides. Thus, for Witepsol® H15 there is reduced the possibility of an interaction between the free hydroxyl groups of the solid fat and the functional groups of the active ingredient molecule.

EXAMPLE 2

Saturation Solubility of Budesonide in the Solid Fat Type Witepsol® H15

The solubility of budesonide was determined in the molten Witepsol® H15 at 40° C. Here, increasing amounts of budesonide were suspended in the solid fat basis. After separation of the undissolved proportion and freezing of the suppository mass the dissolved or undissolved proportion, respectively, was determined with HPLC/UV as follows:

TABLE 2

| Potency of the suppositories/dosage | Proportion of Budesonide dissolved in Witepsol ® H15 |
|---|---|
| 1 mg Budesonide in 1 g Witepsol ® H15 | 0.97 mg/g corresponding to 100% |
| 2 mg Budesonide in 1 g Witepsol ® H15 | 1.47 mg/g corresponding to 75% |

TABLE 2-continued

| Potency of the suppositories/dosage | Proportion of Budesonide dissolved in Witepsol ® H15 |
|---|---|
| 3 mg Budesonide in 1 g Witepsol ® H15 | 1.64 mg/g corresponding to 55% |
| 4 mg Budesonide in 1 g Witepsol ® H15 | 1.65 mg/g corresponding to 42% |

Accordingly, the saturation concentration of budesonide in Witepsol® H15 determined at 40° C. is ca. 1.5 mg/g. In a 1 g suppository with a dosage of 2 mg budesonide 75% of the active ingredient are molecularly disperse dissolved in the solid fat basis, with a dosage of 4 mg these are 55%. Thus, the budesonide suppositories according to the invention are a blend of a solution and a suspension preparation. Only the dissolved proportion of budesonide has to be stabilized by the addition of antioxidants.

To determine the saturation concentration of budesonide in Witepsol® H15 a 1 g suppository was prepared with different budesonide dosages and left for a period of 24 hours at 40° C. Subsequently, there was performed a centrifugation (10 minutes at 4000 rpm) to sediment undissolved budesonide. Finally, the suppositories were hardened for 2 hours in a refrigerator (2-8° C.). To determine the budesonide concentration the suppositories were divided in two different ratios (lower part with suppository tip and upper part). The two parts were individually processed for HPLC assay and then analyzed. From the individual weighed portions as well as the obtained content values the budesonide concentration was calculated in mg/g. The dissolved proportion of budesonide distributes homogenously in the suppository basis, while the undissolved proportion accumulates in the suppository tip. Thus, the results of the budesonide assay in the upper part of the suppositories represent the dissolved proportion of budesonide. These values are found in the table.

EXAMPLE 3

Choice of a Suitable Antioxidant for the Stabilization of Dissolved Budesonide in the Solid Fat Type Witepsol® H15

For the selection attempts different antioxidants described in the prior art were tested. Here, budesonide 2 mg suppositories with a mass of 1.8 g were used that contain the active ingredient completely dissolved in the solid fat basis. The antioxidants were added in a concentration of 100 ppm of the preparation. The control batch was free from antioxidant. As the casting molds laminated films consisting of polyvinylchloride films (PVC) coated with low density polyethylene (LDPE) were used that did not contain an additional barrier layer of polyvinylidene chloride (PVdC). The suppositories were stored at 30° C./65% relative humidity for a period of 30 days. After preparation and storage the contamination profile of the budesonide suppositories was determined with HPLC/UV. The following two tables summarize the tested formulations as well as the results.

TABLE 3

| | Batch: | | | |
|---|---|---|---|---|
| Composition: | V1912 | V1915 | V1916 | V1917 |
| Budesonide, micronized[1] | 2 mg | 2 mg | 2 mg | 2 mg |
| Ascorbyl Palmitate | 0.180 mg (100 ppm) | — | — | — |
| DL-α-Tocopherol | — | 0.180 mg (100 ppm) | — | — |
| Butylated Hydroxyanisole | — | — | 0.180 mg (100 ppm) | — |
| Witepsol ® H15 | 1797.820 mg | 1797.820 mg | 1797.820 mg | 1798.000 mg |
| Suppository Mass | 1800.000 mg | 1800.000 mg | 1800.000 mg | 1800.000 mg |

[1]Particle size distribution: 100% < 10 μm, ≥ 95% < 5 μm, ≥ 80% < 3 μm

TABLE 4

| Batch: | V1917 (control) | | V1912 (100 ppm ascorbyl palmitate) | | V1915 (100 ppm DL-α-tocopherol) | | V1916 (100 ppm butylated hydroxyanisole) | |
|---|---|---|---|---|---|---|---|---|
| Storage period at 30° C./65% rel. humidity in days | 0 | 30 | 0 | 30 | 0 | 30 | 0 | 30 |
| Sum of degradation products (%) | 1.34 | 6.03 | 0.73 | 0.65 | 2.13 | 14.10 | 1.89 | 15.52 |
| Increase during storage (%) | | 4.69 | | — | | 11.97 | | 13.63 |

Without the addition of an antioxidant (control batch, batch V1917) a budesonide degradation of ca. 5% can be observed within 30 days at 30° C./65% relative humidity (see also example 1). The addition of 100 ppm DL-α-tocopherol and butylated hydroxyanisole does not lead to a stabilization of the suppositories (see batches V1915 and V1916). Surprisingly, the degradation of the active ingredient in the presence of these antioxidants even increases significantly. Thus, DL-α-tocopherol and butylated hydroxyanisole do not represent options for the stabilization of the budesonide suppositories. In contrast, ascorbyl palmitate shows a significant anti-oxidative effect. During the storage period no degradation of budesonide can be observed. The experiment is performed under conditions that are unfavorable for the budesonide stability such as complete solubility of the active ingredient in the solid fat as well as the use of cast films without any further oxygen barrier to be able to show the anti-oxidative effect of ascorbyl palmitate.

EXAMPLE 4

Optimum Concentration of Ascorbyl Palmitate as an Antioxidant for the Stabilization of Dissolved Budesonide in the Solid Fat Type Witepsol® H15

The effect of ascorbyl palmitate as an antioxidant for the stabilization of budesonide was tested with the following recipes of budesonide 2 mg suppositories:

TABLE 5

| Composition: | Batch: | | |
| --- | --- | --- | --- |
| | V2035 | V2034 | V2036 |
| Budesonide, micronized[1] | 2 mg | 2 mg | 2 mg |
| Ascorbyl Palmitate | 0.075 mg (75 ppm) | 0.100 mg (100 ppm) | 0.125 mg (125 ppm) |
| Witepsol ® H15 | 997.925 mg | 997.900 mg | 997.875 mg |
| Suppository Mass | 1000.000 mg | 1000.000 mg | 1000.000 mg |

[1]Particle size distribution: 100% < 10 μm, ≥ 95% < 5 μm, ≥ 80% < 3 μm

Thus, for all suppositories the proportion of budesonide dissolved in the solid fat basis and to be stabilized is 75%. As the casting molds laminated films of LDPE/PVC/PVdC were used. After manufacture and storage of 24 months at 25° C./60% relative humidity the contamination profile of the budesonide suppositories was determined with HPLC/UV. The results obtained were as follows:

TABLE 6

| Batch: | V2035 (75 ppm ascorbyl palmitate) | | V2034 (100 ppm ascorbyl palmitate) | | V2036 (125 ppm ascorbyl palmitate) | |
| --- | --- | --- | --- | --- | --- | --- |
| Storage Period in Months | 0 | 24 | 0 | 24 | 0 | 24 |
| Sum of Degradation Products (%) | 0.19 | 2.93 | 0.16 | 2.17 | 0.19 | 1.70 |
| Increase during Storage (%) | | 2.74 | | 2.01 | | 1.51 |

Ascorbyl palmitate stabilizes the budesonide molecularly disperse dissolved in the solid fat basis depending on the concentration. The preferred embodiment of budesonide 2 mg and 4 mg suppositories contains ascorbyl palmitate in a concentration range of 100 ppm to 150 ppm.

EXAMPLE 5

Qualitative and Quantitative Composition of the Preferred Embodiments of Budesonide 2 mg and 4 mg Suppositories

TABLE 7

| | Composition | |
| --- | --- | --- |
| Budesonide, micronized[1] | 2 mg | 4 mg |
| Ascorbyl Palmitate | 0.10-0.15 mg (100-150 ppm) | 0.10-0.15 mg (100-150 ppm) |
| Witepsol ® H15 | 997.85-997.900 mg | 995.85-995.90 mg |
| Suppository Mass | 1000.00 mg | 1000.00 mg |
| Casting Mold | cast film of LDPE/PVC/PVdC | cast film of LDPE/PVC/PVdC |

[1]Particle size distribution: 100% < 10 μm, ≥ 95% < 5 μm, ≥ 80% < 3 μm

EXAMPLE 6

Shelf Life Tests of the Preferred Embodiments of Budesonide 2 mg and 4 mg Suppositories Budesonide 2 mg and 4 mg suppositories were prepared in the preferred embodiment with 100 ppm ascorbyl palmitate and stored at 25° C./60% relative humidity for shelf life tests. After manufacture and in regular intervals during the storage the content and the purity of the suppositories were determined with HPLC/UV. The two following tables summarize the results for budesonide 2 mg suppositories and budesonide 4 mg suppositories.

TABLE 8

Budesonide 2 mg Suppositories with 100 ppm Ascorbyl Palmitate, Batch V2042

| | Storage Period (Months) at 25° C./60% rel. Humidity | | | | | | |
| --- | --- | --- | --- | --- | --- | --- | --- |
| | 0 | 3 | 6 | 9 | 12 | 18 | 24 |
| Content of Budesonide (%) | 99.5 | 97.3 | 96.2 | 96.5 | 96.0 | 95.0 | 96.6 |
| Sum of Degradation Products (%) | 0.16 | 0.09 | 0.16 | 0.27 | 0.36 | 0.72 | 0.86 |

TABLE 9

Budesonide 4 mg Suppositories with 100 ppm Ascorbyl Palmitate, Batch V2043

| | Storage Period (Months) at 25° C./60% rel. Humidity | | | | | | |
| --- | --- | --- | --- | --- | --- | --- | --- |
| | 0 | 3 | 6 | 9 | 12 | 18 | 24 |
| Content of Budesonide (%) | 99.4 | 99.0 | 99.6 | 99.6 | 98.0 | 98.0 | 97.6 |
| Sum of Degradation Products (%) | 0.10 | 0.10 | 0.10 | 0.16 | 0.24 | 0.38 | 0.38 |

The budesonide content and the sum of degradation products change only slightly during storage. With the surprisingly found combination of physical and chemical stabilization the shelf life of the budesonide 2 mg and 4 mg suppositories is ensures for a period of at least 24 months at 25° C./60% relative humidity.

EXAMPLE 7

In Vitro Releasing Tests of Budesonide 2 mg Suppositories

The budesonide suppositories composited and prepared according to the invention release the active ingredient over a period of 2 hours. Within this period, both the proportion of the active ingredient that is suspended and present in a micronized form and the proportion that is molecularly disperse dissolved in the solid fat basis is released. This ensures that the active ingredient is available over a sufficiently long period of time on the rectal mucosa and can exert its therapeutic effect. FIG. 1 shows the releasing profile of budesonide 2 mg suppositories of batch V2042 after manufacture (T0) and after storage of 24 months at 25° C./60% relative humidity (T24). The determination takes place at 37° C., preferably with the flow cell described in the European Pharmacopoeia (apparatus 4), that is operated with a flow rate of 16 ml/min as a closed system. Citric acid phosphate buffer pH 6.8 with an addition of 0.5% sodium dodecyl sulphate is used as the medium. In order to be able to describe the releasing kinetics sampling is performed after 15, 30, 45, 60, 90, and 120 minutes. The budesonide dissolved in the release medium is determined with HPLC/UV.

BRIEF DESCRIPTION OF THE DRAWINGS

FIG. 1 shows the releasing profile of budesonide 2 mg suppositories of batch V2042 after manufacture (T0) and after storage of 24 months at 25° C./60% relative humidity (T24).

EXAMPLE 8

Examination of the Clinical Efficacy and Acceptance of the Suppositories by Patients During a double blind study budesonide suppositories were tested on patients suffering from proctitis. 79 patients in total were treated, wherein different suppositories with different active ingredients were tested without the patients knowing exactly which suppository they received.

During these tests it was found after which period of time a clinical remission, defined as "first day", with 3 defaecations/day, wherein all had to be without blood in the feces, was observed. With the suppositories according to the invention this period was 8 days in median terms.

As a further parameter there was determined the percentage of patients that showed a mucosal healing, wherein this was determined via endoscopy of the affected section of the intestine and was measured as the corresponding part of a disease activity index (modified UC-DAI/Ulcerative Colitis-Disease Activity Index). Said value was 81%. The results obtained with budesonide suppositories according to the invention with 4 mg of active ingredient (1 g total weight) are summarized in table 10 below.

TABLE 10

| Efficacy Parameter | |
|---|---|
| Clinical Remission, defined as first day with ≤ 3 defaecations/day and all without blood in the feces Required Time of Treatment | 8 days |
| Mucosal Healing Endoscopy of the affected section of the intestine, measured as the corresponding part of a disease activity index (modified UC-DAI/Ulcerative Colitis-Disease Activity Index) N/N (%) | 64/79 (81.0%) |

As a further essential aspect that just with suppositories plays an important role there was examined the acceptance of the suppositories according to the invention in patients. Here, data were collected via a corresponding questionnaire, wherein application of the suppositories in the morning and impairment were queried. To the first question, "How do you assess the use of suppositories in the morning?" patients could answer with "easy/not too arduous/difficult". To the second question, "How much did using suppositories in the morning impair your daily routine?" the patients could answer with "considerable/not too much/nearly not at all".

The results of the patient survey are summarized in table 11 below.

TABLE 11

| Patient Acceptance | | | | |
|---|---|---|---|---|
| Application of the Suppositories in the Morning | | | | |
| | easy | not too arduous | difficult | no statement |
| N/N (%) | 62/79 (78.5) | 12/79 (15.2) | 2/79 (2.5) | 3/79 (3.8) |
| Impairment of the everyday life by the Application of the Suppositories in the Morning | | | | |
| | nearly not at all | not too much | considerable | no statement |
| N/N (%) | 46/79 (58.2) | 26/79 (32.9) | 4/79 (5.1) | 3/79 (3.8) |

In summary, it can be concluded that a majority of the patients (78.5%) judged the application in the morning as easy and simple. Moreover, the majority of the patients (58.2%) found almost no impairment of the everyday life by the application of the suppositories in the morning.

These data show that the suppositories according to the invention are not only storage-stable, but also have a very good clinical efficacy with simultaneous high acceptance by the patients.

The invention claimed is:

1. A pharmaceutical formulation for rectal administration, containing budesonide or pharmaceutically compatible salt or derivative thereof; at least 80 wt % of a solid fat or a mixture of different solid fats, based on the total weight of the formulation, wherein the solid fat or mixture of different solid fats comprises at least 80 wt % triglycerides, a hydroxyl value of 1 to 15 and less than 1 wt % of unsaturated fatty acids; and at least one anti-oxidation agent that is compatible therewith, wherein the budesonide is present in a micronized form, wherein 100% of the particles are smaller than 10 μm per particle.

2. The formulation of claim 1, wherein the formulation has a small distance between melting and freezing point, wherein the melting point is between 33.5° C. and 35.5° C. and the freezing point is between 32.5° C. and 34.5° C.

3. The formulation of claim 1, wherein the formulation comprises at least 85% of the solid fat or mixture of different solid fats.

4. The formulation of claim 1, wherein the formulation comprises at least 90% of the solid fat or mixture of different solid fats.

5. The formulation of claim 1, wherein the formulation comprises at least 95% of the solid fat or mixture of different solid fats.

6. The formulation of claim 1, wherein the formulation comprises at least 99% of the solid fat or mixture of different solid fats.

7. The formulation of claim 1, wherein the formulation is a suppository for anal administration.

8. The formulation of claim 7, wherein the suppository has a weight of about 0.8 g to about 1.2 g.

9. The formulation of claim 1, wherein the formulation comprises 1.8 to 4.2 mg of budesonide.

10. The formulation of claim 9, wherein the formulation comprises 1.8 to 2.2 mg of budesonide.

11. The formulation of claim 9, wherein the formulation comprises 3.8 and 4.2 mg of budesonide.

12. The formulation of claim 1, wherein the at least one anti-oxidation agent comprises ascorbyl palmitate.

13. The formulation of claim 12, wherein the ascorbyl palmitate is present in a concentration of 50 ppm to 200 ppm.

14. The formulation of claim 1, wherein the formulation is prepared under exclusion of oxygen.

15. The formulation of claim 1, wherein the formulation is packaged in the form of suppositories in a gas-tight cast film.

16. A pharmaceutical formulation according to claim 1 for the treatment of inflammatory diseases of the rectum.

17. A pharmaceutical formulation according to claim 1 for the treatment of acute ulcerative proctitis.

18. The formulation of claim 1, wherein the formulation is storage stable at environmental conditions of 25° C./60% relative humidity for at least 24 months.

\* \* \* \* \*